United States Patent
Long et al.

(10) Patent No.: US 7,955,328 B2
(45) Date of Patent: Jun. 7, 2011

(54) TISSUE DISSECTOR AND/OR COAGULATOR WITH A SLIT IN AN INSULATING TIP TO CONTROL THE DIRECTION OF ENERGY

(75) Inventors: Gary Long, Cincinnati, OH (US); Gregory J. Bakos, Mason, OH (US); Omar Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 749 days.

(21) Appl. No.: 11/558,623

(22) Filed: Nov. 10, 2006

(65) Prior Publication Data
US 2008/0114352 A1    May 15, 2008

(51) Int. Cl.
*A61B 18/18* (2006.01)
(52) U.S. Cl. ............................................ 606/46; 606/41
(58) Field of Classification Search ................ 606/41–52
See application file for complete search history.

(56) References Cited

U.S. PATENT DOCUMENTS

| | | | | |
|---|---|---|---|---|
| 1,362,993 | A | | 12/1920 | Hederich |
| 4,003,380 | A | * | 1/1977 | Wien .............................. 606/51 |
| 4,548,207 | A | * | 10/1985 | Reimels .......................... 606/50 |
| 4,593,691 | A | | 6/1986 | Lindstrom et al. |
| 4,657,016 | A | * | 4/1987 | Garito et al. .................... 606/45 |
| 4,840,176 | A | | 6/1989 | Ohno et al. |
| 5,080,660 | A | | 1/1992 | Buelna |
| 5,643,255 | A | * | 7/1997 | Organ ............................. 606/41 |
| 5,885,279 | A | * | 3/1999 | Bretton .......................... 606/41 |
| 5,919,188 | A | * | 7/1999 | Shearon et al. ................. 606/41 |
| 5,919,191 | A | * | 7/1999 | Lennox et al. .................. 606/48 |
| 5,941,876 | A | * | 8/1999 | Nardella et al. ................ 606/45 |
| 6,027,502 | A | * | 2/2000 | Desai .............................. 606/41 |
| 6,066,134 | A | * | 5/2000 | Eggers et al. ................... 606/32 |
| 6,161,543 | A | * | 12/2000 | Cox et al. ...................... 128/898 |
| 6,246,913 | B1 | * | 6/2001 | Sharkey ....................... 607/101 |
| 6,296,640 | B1 | | 10/2001 | Wampler et al. |
| 6,409,727 | B1 | * | 6/2002 | Bales et al. .................... 606/47 |
| 6,579,300 | B2 | | 6/2003 | Griego et al. |
| 6,918,906 | B2 | * | 7/2005 | Long .............................. 606/41 |
| 2002/0095152 | A1 | | 7/2002 | Ciarrocca et al. |
| 2003/0233091 | A1 | * | 12/2003 | Whayne et al. ................ 606/49 |
| 2004/0017201 | A1 | | 1/2004 | Brugger et al. |
| 2004/0167514 | A1 | | 8/2004 | Okada |
| 2005/0261675 | A1 | * | 11/2005 | Shibata .......................... 606/45 |
| 2005/0267332 | A1 | | 12/2005 | Paul et al. |
| 2005/0288667 | A1 | | 12/2005 | Thompson et al. |
| 2007/0179495 | A1 | | 8/2007 | Mitchell et al. |

FOREIGN PATENT DOCUMENTS

WO    2006092565    9/2006

* cited by examiner

*Primary Examiner* — Roy D Gibson
*Assistant Examiner* — Benjamin Lee
(74) *Attorney, Agent, or Firm* — Nutter McClennen & Fish LLP

(57) ABSTRACT

Various devices and methods for dissecting and/or coagulating tissue are provided. In one embodiment, a surgical device is provided that includes an elongate member having proximal and distal ends, an energy emitter coupled to the distal end of the elongate member, and an insulating element that is disposed around the energy emitter. The insulating element can have an opening for receiving energy from the energy emitter, and the opening can be shaped to control a direction of energy emitted from the energy emitter.

18 Claims, 9 Drawing Sheets

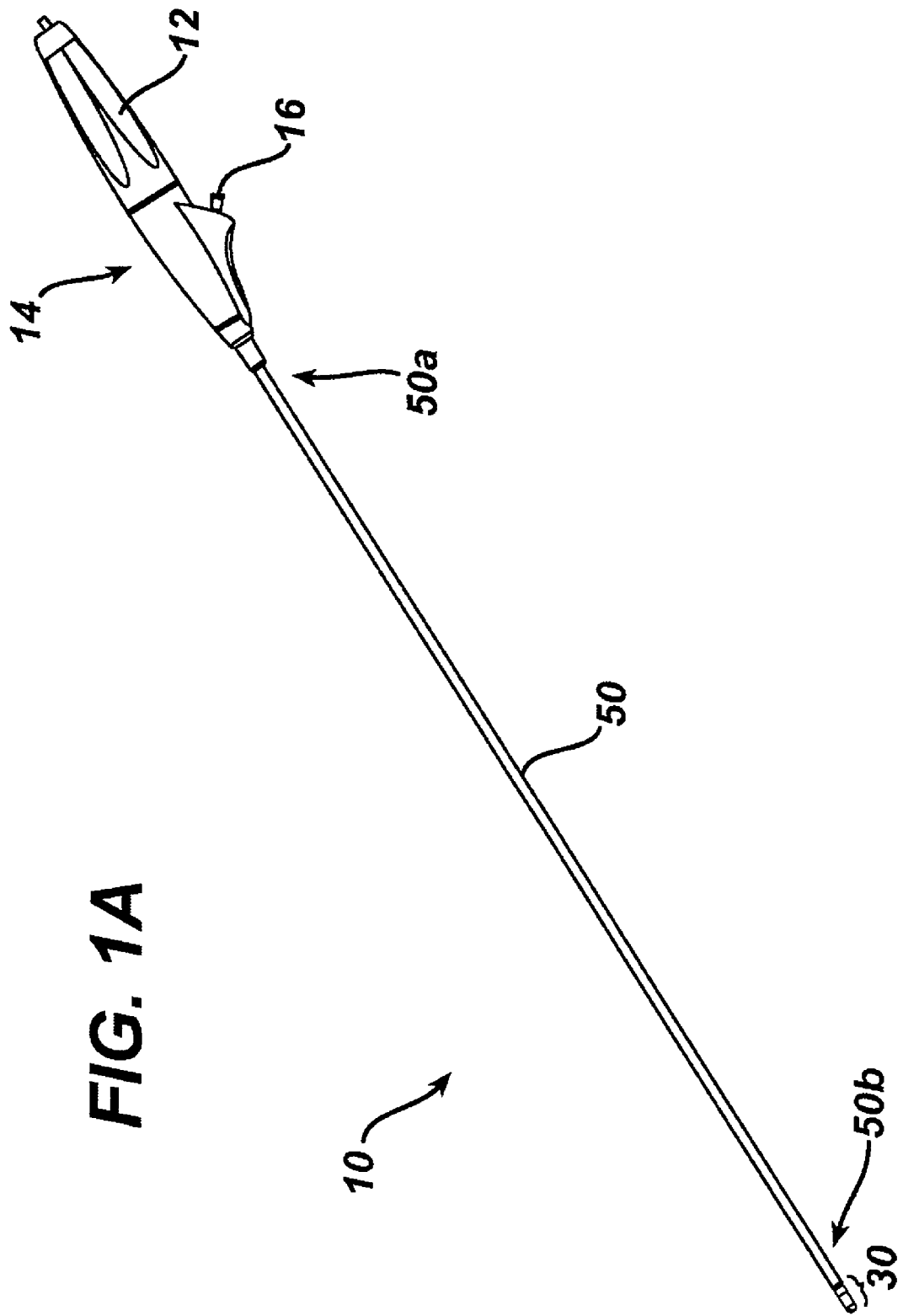

TISSUE DISSECTOR AND/OR COAGULATOR WITH A SLIT IN AN INSULATING TIP TO CONTROL THE DIRECTION OF ENERGY

FIELD OF THE INVENTION

The present invention relates to surgical devices, and in particular to devices and methods for cutting tissue.

BACKGROUND OF THE INVENTION

Laparoscopic surgery is one type of minimally invasive surgery in which a surgeon uses a trocar port to access a surgical site within the abdominal cavity of a patient. The benefits of laparoscopic surgery, as compared to open surgery, include less pain, shorter recovery time, less scarring, and lower cost.

One common type of laparoscopic surgery is a cholecysetctomy, or the removal of the gall bladder. In general, a laparoscopic cholecystectomy requires several small incisions in the abdomen to allow for the insertion of surgical instruments as well as a video camera for viewing the surgical site. Once the instruments and the camera are positioned at or near the surgical site, the gall bladder is located and separated from its connective tissues to allow for removal from the patient. Common separation techniques include cutting the tissues with a device that uses a high frequency current, such as a monopolar hook or paddle. While effective, such a cutting device can deliver energy in all directions, causing the tissues which surround the targeted tissues to become inadvertently damaged. The same issue can also arise in other laparoscopic procedures that require the cutting of tissue.

Endoscopic surgery affords another minimally invasive way to access the abdominal cavity in which access is obtained via natural openings such as the mouth or anus. Many types of endoscopic procedures require the separation of tissues. Similar to laparoscopic procedures, common separation techniques for endoscopic procedures include cutting the tissues with a device that uses a high frequency current, e.g., a needle knife device. However, as noted above, such a device can cause inadvertent damage to tissues that surround the targeted tissue.

Accordingly, there remains a need for improved methods and devices for dissecting and/or coagulating tissue.

SUMMARY OF THE INVENTION

Disclosed herein are devices and methods for dissecting and/or coagulating tissue. In one embodiment, a surgical device is provided that includes an elongate member having proximal and distal ends, an energy emitter coupled to the distal end of the elongate member, and an insulating element that is disposed around the energy emitter. The insulating element can have an opening for receiving energy therethrough from the energy emitter, and for controlling a direction of energy emitted from the energy emitter. In an exemplary embodiment, the energy emitter can be recessed within the opening. The device can also include an electrical connector that extends through the elongate member and that is coupled to the energy emitter to deliver energy to the energy emitter. An insulating sheath can be disposed around the electrical connector.

The energy emitter and insulating element can have a variety of configurations. In one embodiment the energy emitter can be in the form of an electrode having an elongate substantially planar tip, and the insulating element can include an opening in the form of an elongate slit formed in a distal end of the insulating element. In another embodiment, the energy emitter can be in the form of an electrode having a hook-shaped distal tip, and the opening in the insulating element can be in the form of a hook-shaped cut-out formed in a sidewall thereof.

In another embodiment, the device can include a fluid lumen that is formed within or alongside the elongate member and that is adapted to deliver fluid to tissue surrounding the insulating element. The device can also include an opening that is located adjacent to the distal end of the insulating sheath for delivering fluid to tissue, and a handle having a fluid port that is coupled to the fluid lumen. The device can also include other features. For example, the distal end of the insulating element can be blunt. The energy emitter and the insulating element can also be rotatable relative to the elongate member to facilitate positioning thereof.

In another embodiment, an endoscopic tissue resecting device is provided that includes an elongate flexible shaft adapted to be inserted through a tortuous body lumen, and an energy delivering electrode located at the distal end of the elongate shaft. The device can also include an insulating tip that surrounds the electrode and that has an opening formed therein for receiving energy from the electrode therethrough. The opening can be configured to control a direction of energy delivery.

Methods for dissecting and/or coagulating tissue are also provided. In one embodiment, a method for dissecting tissue includes positioning an energy emitter assembly located on a distal end of an elongate shaft adjacent to tissue to be treated. The energy emitter assembly can include an electrode surrounded by an insulating element. The method can also include activating the energy emitter assembly to deliver energy from the electrode through an opening formed in the insulating element to dissect and/or coagulate the tissue. The opening can have a variety of configurations that are effective to control a direction of the energy delivered therethrough. In one embodiment, the opening can be in the form of an elongate slit that is formed in a distal end of the insulating element. In another embodiment, the opening can be in the form of a hook-shaped cut-out that is formed in a distal end of the insulating element. The method can also optionally include rotating the energy emitter assembly relative to the elongate shaft such that the opening is positioned adjacent to the tissue to be dissected and/or coagulated. In other embodiments, the method can include delivering fluid through a lumen formed through the elongate shaft to tissue surrounding the insulating element. Additionally or alternatively, the method can include pressing a blunt distal end of the insulating element against the tissue to manipulate the tissue.

BRIEF DESCRIPTION OF THE DRAWINGS

The invention will be more fully understood from the following detailed description taken in conjunction with the accompanying drawings, in which:

FIG. 1A is a perspective view of one embodiment of a device for dissecting and/or coagulating tissue;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for dissecting and/or coagulating tissue. In general, a device is provided having an energy emitter assembly with an energy emitter that is contained within an insulating tip. The insulating tip can have an opening formed therein that is effective to control a direction of energy emitted from the energy emitter. In use, the opening can be positioned adjacent to a tissue to be dissected and/or coagulated, and energy can be delivered to the electrode whereby the energy will flow through the opening. As a result, the energy is delivered to the target tissue while the tissues surrounding the target tissue are insulated from the energy and thus from any incidental damage. The device can be used in any open, laparoscopic or endoscopic procedure which requires the dissection and/or coagulation of tissue, such as a cholecystectomy, gastric restriction, an appendectomy, and liposuction, submucosal tunneling, among others. It may also be used to coagulate tissue in cases such as gastric antral vascular ectasia (also known as GAVE or watermelon stomach), and Barrett's esophagus. The device may also be used to stop bleeding, such as from ulcers or bleeding vessels. A person skilled in the art will also appreciate that the present invention has applications in conventional endoscopic and open surgical instrumentation as well applications in robotic-assisted surgery. The device can also be modified to coagulate and/or ablate tissue without cutting the tissue.

Figure 1B:
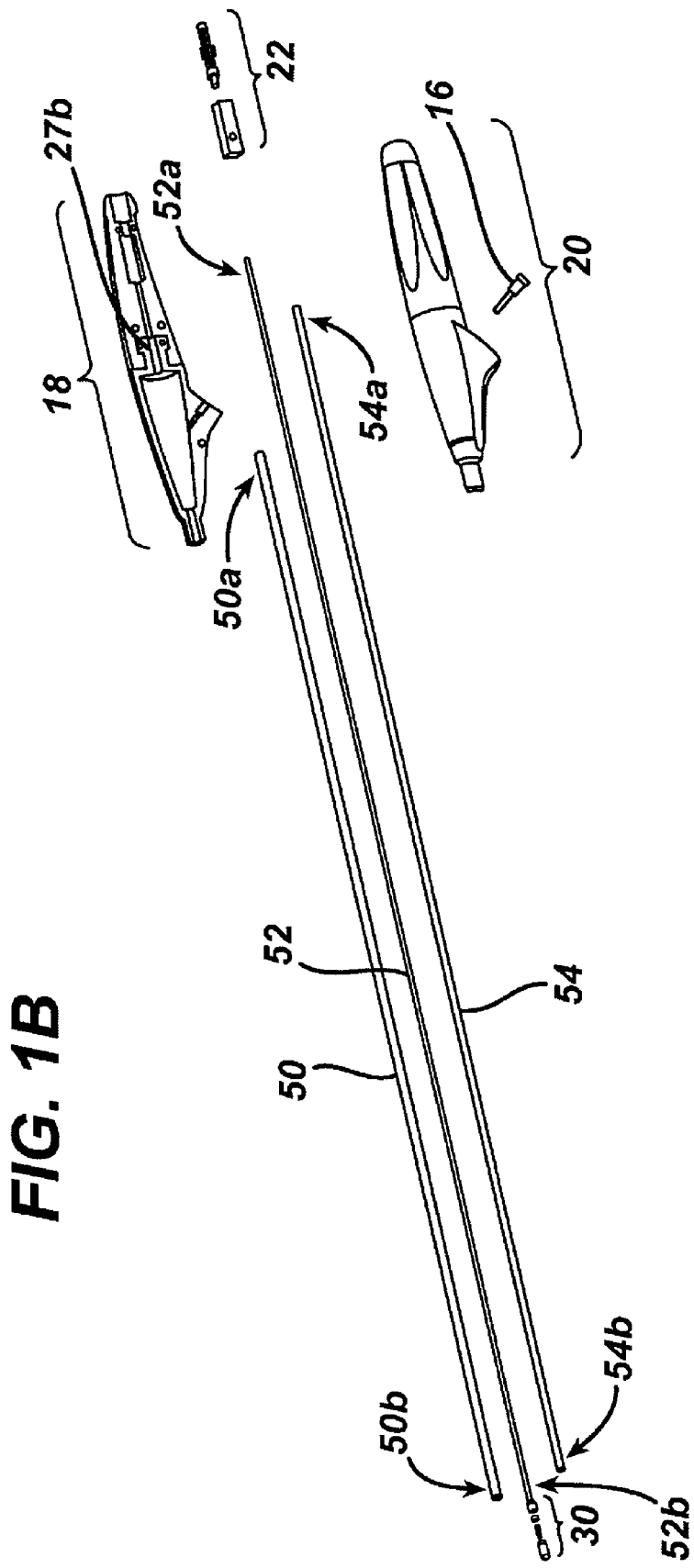
FIG. 1B is an exploded view of the device of FIG. 1A.
Figure 2A:
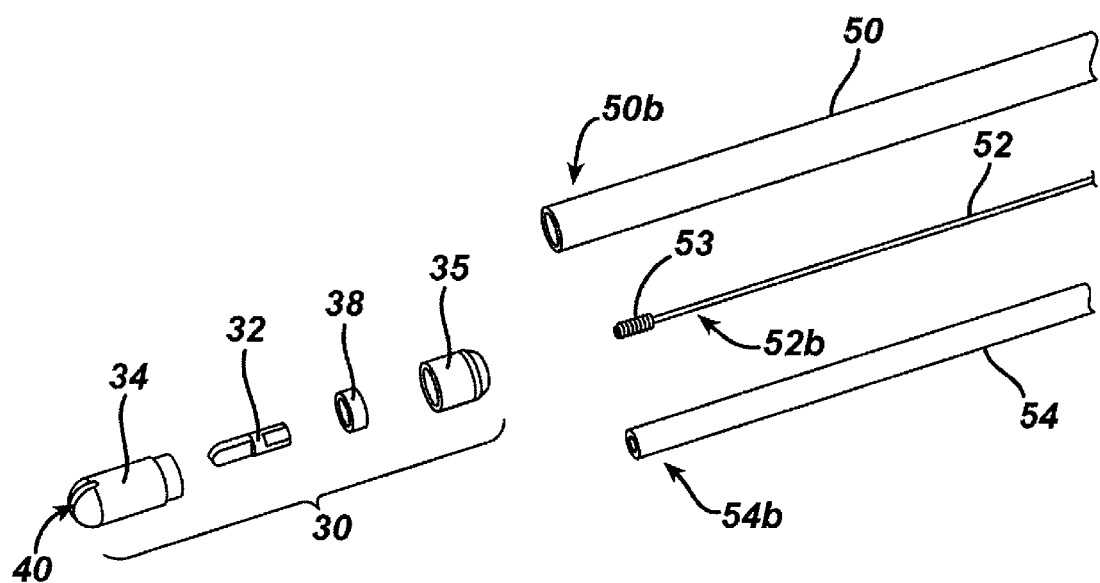
FIG. 2A is an exploded view of a distal end of the device FIG. 1A.

FIGS. 1A-1B illustrate one exemplary device 10 for dissecting and/or coagulating tissue. The device 10 generally includes a flexible outer tube 50 having proximal and distal ends 50a, 50b. An energy emitter assembly 30 is located adjacent to the distal end 50b of the outer tube 50, and as shown in FIG. 2A it includes an energy emitter 32 that is disposed within an insulating tip 34. The insulating tip 34 has an opening 40 that is formed therein for controlling a direction of energy delivered to tissue. The device 10 can also include a handle 14 located adjacent to the proximal end 50a of the outer tube 50 for manipulating the device 10. The handle 14 can include features for coupling to an energy source as well as various other features for facilitating the dissection and/or coagulation of tissue.

Figure 2B:
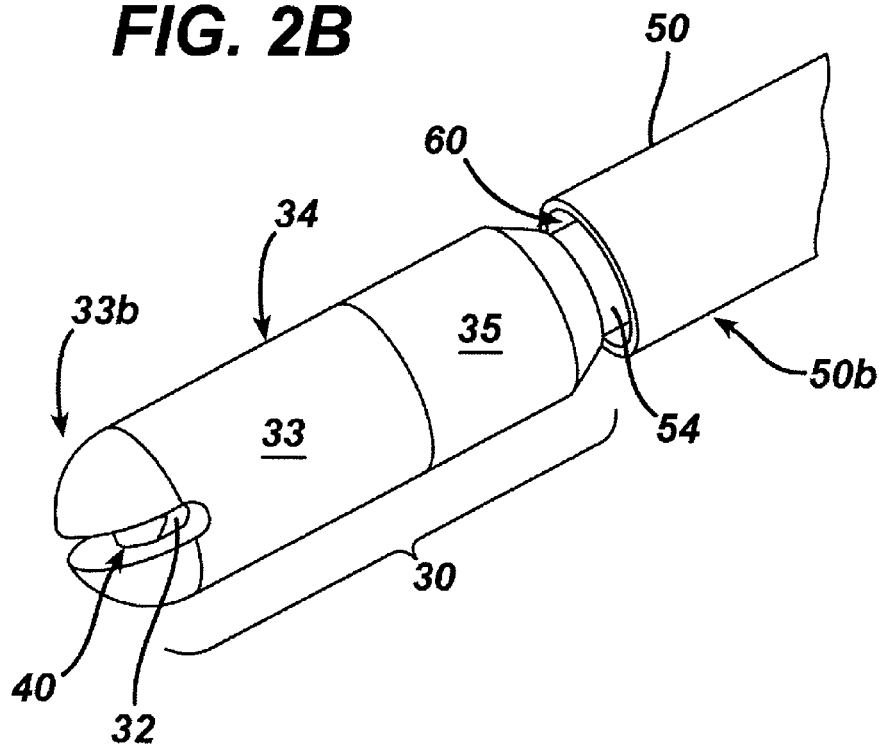
FIG. 2B is a perspective view of the distal end of the device of FIG. 1A.
Figure 2C:
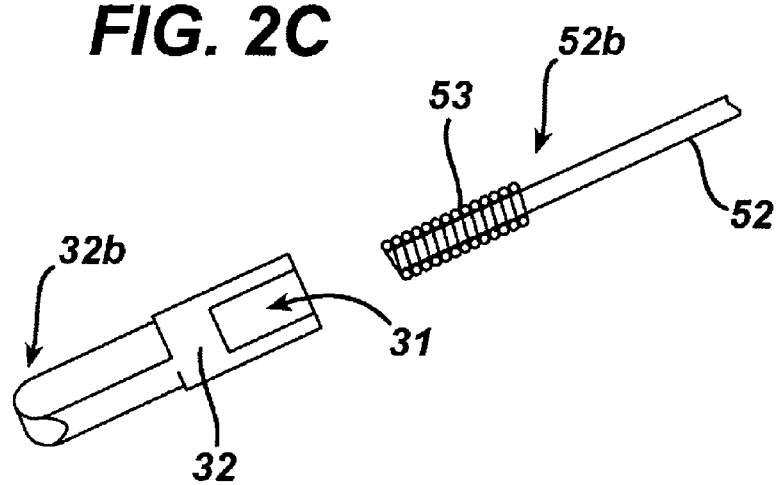
FIG. 2C is an exploded view of a distal end of an electrode and a wire of the device of FIG. 1A.
Figure 2D:
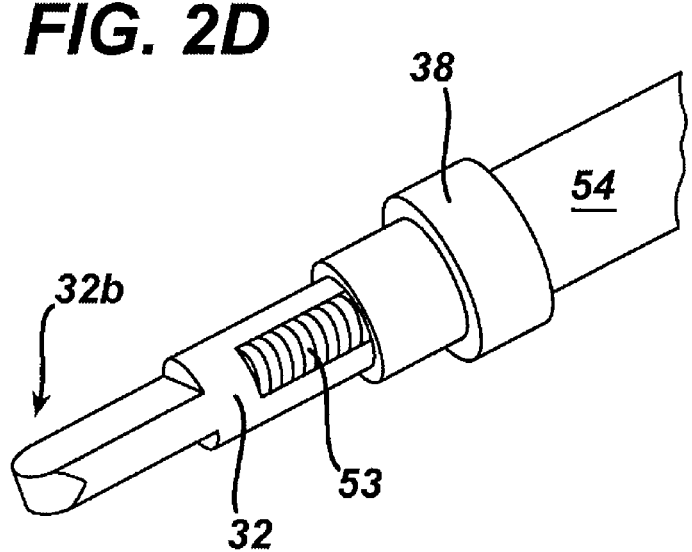
FIG. 2D is a perspective view of the distal end of an electrode and an insulating sheath of the device of FIG. 1A.

FIGS. 2A-2E illustrate the energy emitter assembly 30 in more detail. As shown in FIGS. 2A and 2B, the energy emitter assembly 30 generally includes an energy emitter 32 that is contained within an insulating tip 34. The energy emitter 32 can be any device that is adapted to deliver energy to tissue, such as an electrode. A variety of electrodes can be used, and the electrode can be adapted to deliver RF, monopolar, bipolar, or any other type of energy to the tissue depending upon the needs of the user. The energy emitter can also have a variety of configurations. FIGS. 2A, 2C, and 2D illustrate an energy emitter 32 that has a generally elongate shape with a distal portion that is in the form of a substantially planar tip 32b, and a proximal portion that is adapted to couple to a wire 52 for delivering energy to the energy emitter 32.

Figure 2E:
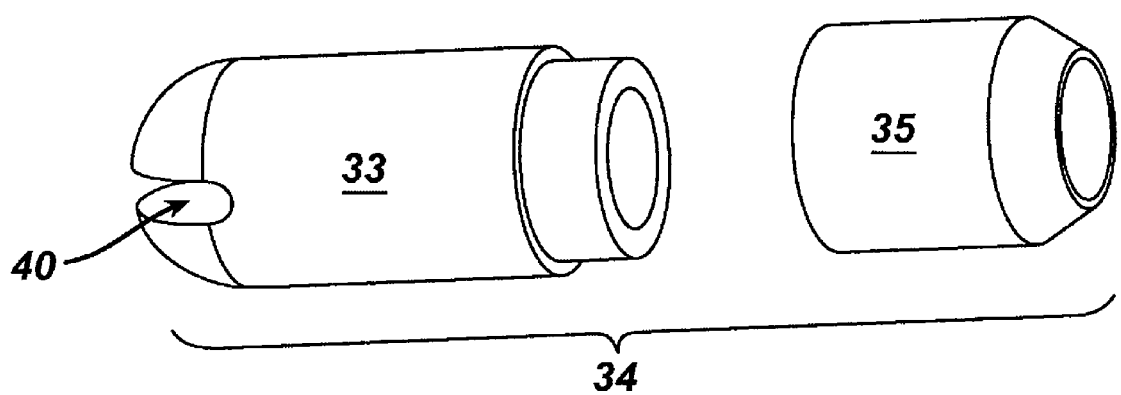
FIG. 2E is an exploded view of the insulating tip of the device of FIG. 1A.

As indicated above, the energy emitter 32 is disposed within an insulating tip 34 that is effective to control the direction of energy that is emitted from the energy emitter 32. While the insulating tip 34 can have a variety of configurations, in the embodiment shown in FIGS. 2A, 2B, and 2E the insulating tip 34 is in the form of a substantially cylindrical hollow housing that receives the energy emitter 32 therein. The cylindrical configuration can be effective to facilitate insertion of the tip 34 through a body lumen. The insulating tip 34 can have a unitary configuration, or it can include proximal and distal portions 33, 35 that are adapted to mate together as shown in FIG. 2E. The proximal and distal portions 33, 35 can be mated to one another using any technique known in the art, such as an interference fit, a threaded connection, welding, etc. The proximal portion 35 of the insulating tip 34 can be adapted to connect to at least a portion of an insulating sheath 54, as will be discussed in more detail below. The distal portion 33 of the insulating tip 34 can have a distal end 33b that is blunt to allow the tip 34 to be used to manipulate tissue. As shown in FIG. 2E, the distal-most end is rounded. A person skilled in the art will appreciate that the insulating tip 34 can have a variety of other shapes and sizes, and that the particular configuration can vary depending on the configuration of the energy emitter. The insulating tip 34 can also be formed from a variety of insulating materials, such as a ceramic, silicon, or other high temperature materials.

As previously indicated, the insulating tip 34 can also include an opening formed therein for controlling a direction of energy delivering from the energy emitter 32. While the opening can be formed at various locations, and it can have a variety of configurations, shapes, and sizes that correspond to a desired energy delivery pattern, in the embodiment shown in FIGS. 2B and 2E the opening 40 is in the form of an elongate slit that is formed in the distal end 33b of the distal portion 33 of the insulating tip. The opening 40 extends in a direction that is substantially perpendicular to a longitudinal axis of the device, such that it extends between opposed sidewalls of the insulating tip 34. The opening 40 can also have a variety of sizes, however in an exemplary embodiment it has a width of about 1 mm. In use, the opening 40 is effective to project energy from the distal end 33b of the insulating tip 34 to tissue, as will be discussed in more detail below.

When the energy emitter 32 and insulating tip 34 are assembly, the energy emitter 32 is preferably recessed within the insulating tip 34 such that the energy emitter 32 does not extend into or through the opening 40. The distance that the energy emitter 32 is recessed within the insulating tip 34 can vary, however in one embodiment the energy emitter 32 can be located approximately 1 mm from tissue when the insulating tip 34 is placed against tissue. As a result, energy emitted from the energy emitter 32 can have an arc configuration upon exiting the opening 40. The formation of this arc is effective to facilitate the flow of current into the tissue without the electrode making direct contact with the tissue being cut or coagulated. In one embodiment, this arc may be obtained using monopolar output from an electrosurgical generator in a setting that produces a voltage high enough to form plasma in air across the distance between the electrode and the tissue.

Figure 3A:
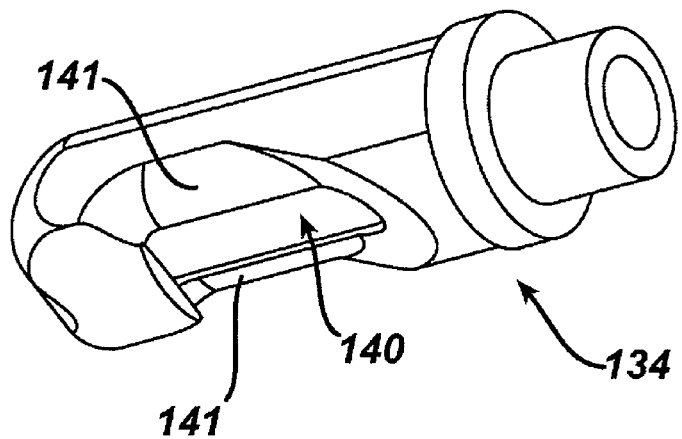
FIG. 3A is a perspective view of another embodiment of an electrode and an insulating tip of a device for dissecting and/or coagulating tissue.
Figure 3B:
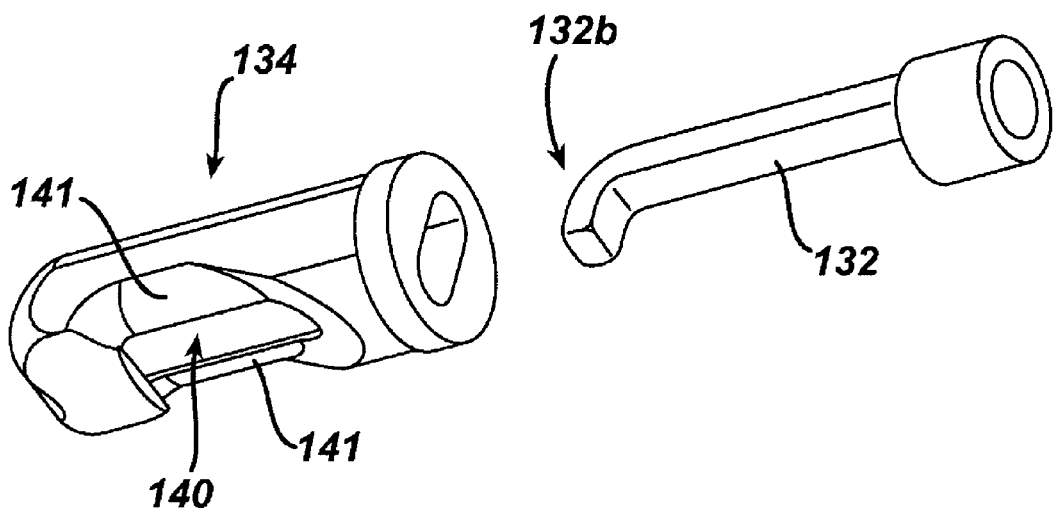
FIG. 3B is an exploded view of the electrode and insulating tip of FIG. 3A.

As indicated above, the energy emitter and insulating tip can have a variety of other configurations, shapes, and sizes. FIGS. 3A-3B illustrate another embodiment of an energy emitter assembly 130 having an energy emitter 132 that is recessed within an insulating tip 134. The energy emitter 132 is similar to the energy emitter 32 of FIGS. 2A-2E, however it has a curved or hook-shaped distal portion 132b. The insulating tip 134 is also similar to the insulating tip 34 of FIGS. 2A-2E, however it has an opening 140 that is formed in the sidewall 141 thereof and that extends longitudinally along the tip 34. The opening 140 can also have a hook-shaped configuration that conforms to the shape of the energy emitter 132. In use, the opening 140 is effective to project energy from a sidewall 141 of the insulating tip 134 to tissue.

A variety of techniques can be used to deliver energy to the energy emitter. In one embodiment, a wire 52 can extend between the handle 14 and the energy emitter 32. The proximal end of the wire 52a can be coupled to a connector 22 disposed within the handle 14. The connector 22 can be adapted to mate to an energy delivery device to deliver energy to the wire 52, as will be discussed in more detail below. The distal end 52b of the wire 52 can be mated to the energy emitter 32. While various mating techniques can be used, in an exemplary embodiment the distal end of the wire 52 can include an electrical connector 53 that is adapted to fit within a bore 31 formed within the energy emitter 32. The device can also include an insulating sheath 54 that surrounds the wire 52, extending from the handle 14 and through the elongate member 12 to cover the entire length of the wire 52. The distal end 54b of the insulating sheath 54 can be attached to the insulating tip 34 using a connector, such as a coupling or sleeve 38, as shown in FIG. 2D. In particular, the sleeve 38 can extend around the insulating sheath 54 and it can be coupled to the proximal portion 35 of the insulating tip 34. The sleeve 38 will thus facilitate positioning of the energy emitter 32 within the insulating tip 34. The sleeve 38 can also allow the insulating tip 34 to rotate with the insulating sheath 54, as will be discussed below. While FIG. 2D illustrates a sleeve 38, a variety of other techniques that can be used to mate the insulating tip 34 and the insulating sheath 54.

One skilled in the art will appreciate that the wire 52 and the insulating sheath 54 can have a variety of configurations, but in an exemplary embodiment they are flexible or semi-flexible to allow the device 10 to be introduced translumenally, e.g., through a natural orifice. The flexibility of the wire 52 and the insulating sheath 54 can vary along different portions of the wire 52 and/or the insulating sheath 54 depending upon the intended use. The wire may also be a flexible torque cable to transmit torque from a proximal end to the distal end.

Figure 4A:
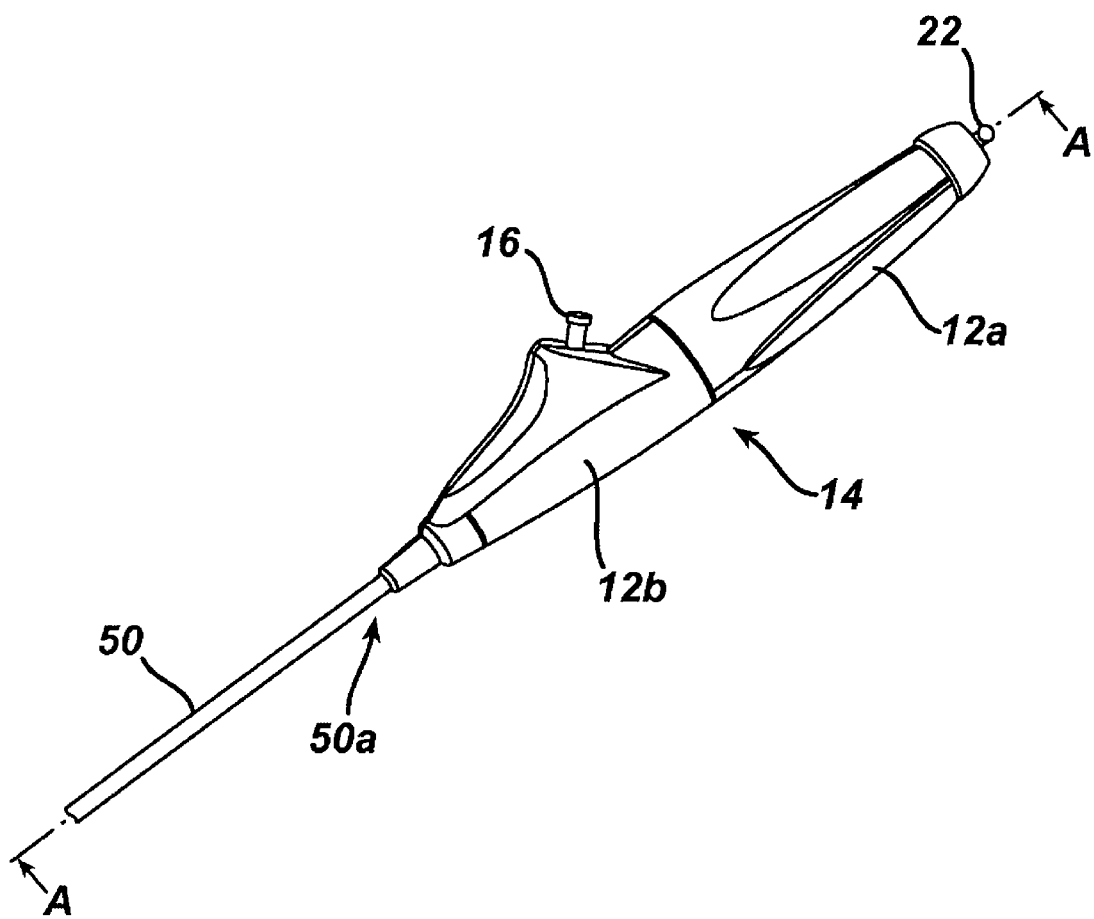
FIG. 4A is a perspective view of a proximal end of the device of FIG. 1A.
Figure 4B:
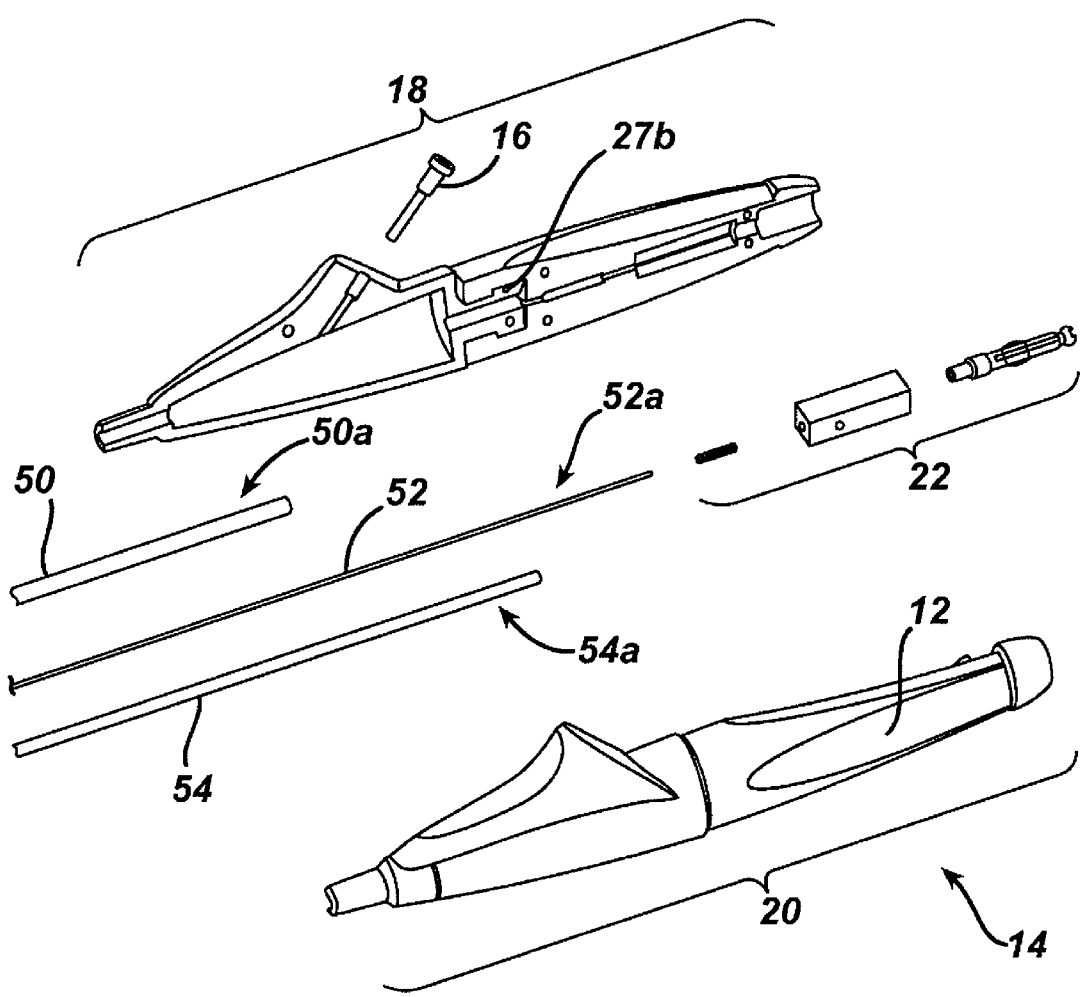
FIG. 4B is an exploded view of the device of FIG. 4A.
Figure 4C:
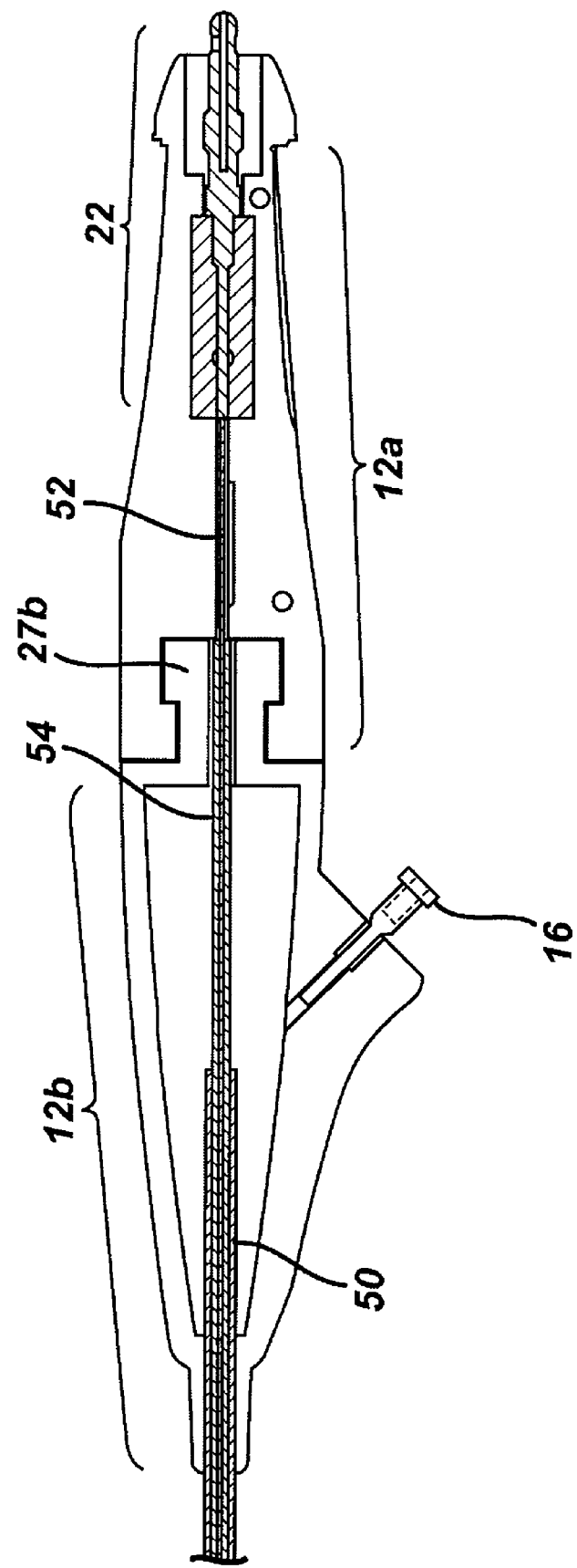
FIG. 4C is a cross-sectional view taken across line A-A of the device of FIG. 4A.

As previously indicated, the device 10 can also include a handle 14 is located on the proximal end 50a of the outer tube 50 to facilitate manipulation and handling of the device 10. The handle 14 can have any configuration that allows a user to conveniently hold and operate the device 10. As shown in FIGS. 4A-4C, the handle 14 is formed from first and second housing halves 18, 20 that mate together to form a substantially elongate generally cylindrical member. The handle 14 can be adapted to facilitate the delivery of energy through the wire 52 to the energy emitter 32. In the illustrated embodiment, the handle 14 includes a connector 22 that is adapted to couple the wire 52 to an external energy source, such as a generator or an electrical outlet. The handle can also include a mechanism for activating energy delivery of the wire, such as a button or knob (not shown). Alternatively, an energy source (not shown), such as a battery operated high frequency, high voltage source that is in electrical communication with the wire, can be disposed within the handle.

The energy emitter assembly 30 can also be adapted to rotate such that the opening 40 in the insulating tip 34 can be positioned adjacent to the tissue to be dissected and/or coagulated. While a variety of techniques can be used, as best shown in FIG. 4C the handle 14 can include a proximal rotatable portion 12a that is coupled to and rotates relative to a distal stationary portion 12b. FIG. 4C illustrates a base 27b for rotatably coupling the proximal and distal portions 12a, 12b of the handle 14. The connector 52, which is mated to the proximal end 52a of the wire 52 and the proximal end 54a of the insulating sheath 54, is mated to the proximal rotation portion 12a. Thus, rotation of the rotatable portion 12a relative to the stationary portion 12b will apply a torque to and cause corresponding rotation of the insulating sheath 54 and wire 52. As a result, the energy emitting assembly 30 coupled to the distal end 54b of the insulating sheath 54 and the distal end 52b of the wire 52 will rotate. The outer tube 50, which will be discussed in more detail below, can optionally be fixedly mated to the distal stationary portion 12b of the handle 14, such that the insulating sheath 54 and wire 52 rotate within the outer tube 50. Alternatively, the handle 14 can include sliding actuator levers, a trigger, or other mechanisms that can be used to selectively rotate the insulating sheath, wire, and energy emitter assembly.

In another embodiment, the device can be adapted to deliver fluid to the tissue site. While various techniques can be used, in one embodiment the device can include an outer tube 50 that surrounds the insulating sheath 54. The outer tube 50 can have a variety of configurations, but in an exemplary embodiment it can be flexible or semi-flexible to allow the device 10 to be introduced translumenally, e.g., through a natural orifice. The flexibility of the outer tube 50 can vary along different portions of the outer tube 50 depending upon the needs of the user. The proximal end 50a of the outer tube 50 can be coupled to a fluid inlet port 16 formed in the handle 14, and the distal end 50b of the outer tube 50 can terminate just proximal to the proximal portion 35 of the insulating tip 34 to form a fluid outlet port, as shown in FIG. 2B. The outer tube 50 can have a variety of sizes, however in an exemplary embodiment, the outer tube 50 has an inner diameter that is greater than an outer diameter of the insulating sheath 54 such that a fluid lumen 60 is formed between the outer tube 50 and the insulating sheath 54. In use, fluid can be delivered through the fluid lumen 60 to the target site. The fluid can then flow around the insulating tip 34 to wash away debris, cool the tissue, and reduce the amount of char formation, etc. While the illustrated device 10 includes a single lumen 60 for the delivery of fluid, separate or additional lumens could be added depending on the intended use of the device.

As previously indicated, the device 10 can be used to perform a variety of medical procedures. In an exemplary embodiment, however, the device 10 is preferably used in endoscopic procedures whereby the device 10 is inserted into a tortuous lumen to a target site. As noted above, the outer tube 50, insulating sheath 54, and wire 52 can passively flex and bend in response to the lumen. The device 10 can also optionally be used in conjunction with an endoscope for providing illumination and visualization of the surgical site.

Alternatively, the surgical site can be viewed using an onboard optics system that is incorporated into the device 10.

Once the energy emitter assembly 30 is positioned adjacent to the target tissue, if necessary the blunt distal end 33b of the insulating tip 34 can be used to manipulate tissue in order to gain access to the target tissue and/or to position the energy emitter assembly 30 at the target tissue. Once the energy emitter assembly 30 is positioned adjacent to the target tissue, the opening 40 can be oriented to direct energy toward the tissue to be dissected and/or coagulated. In order to facilitate positioning of the opening 40, the energy emitter assembly 30 can be rotated by turning the rotatable portion 12a of the handle 14. This applies a torque to the insulating sheath 54, wire 52, or both, which in turn causes the energy emitter assembly 30 to rotate. Once the opening 40 is oriented toward the tissue to be cut, the generator or energy delivery device can be activated to deliver energy through the wire 52 to the energy emitter 32. Energy will flow through the opening 40, which directs the energy towards the target tissue and controls the desired pattern of energy delivery. For example, wherein the insulating tip 34 has an opening 40 in the form of an elongate slit, as shown in FIG. 2B, the energy will form an elongate cut in the tissue that corresponds to the shape of the opening 40. The insulating tip 34 protects the tissues surrounding the target tissue from incidental damage as the energy is emitted from the opening 40.

Fluid can also be applied to the target site prior to, simultaneously with, or subsequent to the delivery of energy to the target site. For example, fluid can be delivered to the fluid inlet port 16 in the handle 14 where it can flow through the fluid lumen 60, and exit the distal end of the lumen 60. The fluid can flow around the insulating tip 34, as well as into tissue surrounding the tip, thereby washing away debris and clearing smoke from the area. The fluid can also hydrate the tissues, making the tissues easier to dissect and/or coagulate. One skilled in the art will appreciate that a variety of fluids can be delivered to the target site, and the type of fluid delivered can depend on the particular procedure being performed. Exemplary fluids that can be delivered to the surgical site can include electrolyte solutions, such as saline, as well as medicaments.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
an elongate member having proximal and distal ends;
an energy emitter coupled to the distal end of the elongate member;
an insulating element disposed around the energy emitter and having an opening formed therein for receiving energy therethrough from the energy emitter, the energy emitter being recessed within the opening in the insulating element, and the opening being shaped to control a direction of energy emitted from the energy emitter; and
an electrical connector extending through the elongate member and coupled to the energy emitter for delivering energy thereto;
wherein the opening is in the form of a distal-facing elongate slit that is formed in a distal-most end of the insulating element and that extends in a direction substantially perpendicular to a longitudinal axis of the elongate member, such that it extends between opposed sidewalls of the insulating element.

2. The device of claim 1, wherein the energy emitter is an electrode.

3. The device of claim 2, wherein the electrode has an elongate substantially planar tip and the opening comprises an elongate slit formed in a distal end of the insulating element for controlling a direction of energy emitted from the electrode.

4. The device of claim 1, wherein a distal end of the insulating element is blunt.

5. The device of claim 1, further comprising an insulating sheath disposed around the electrical connector.

6. The device of claim 5, further comprising a lumen formed between the elongate member and the insulating sheath and adapted to deliver fluid therethrough.

7. The device of claim 6, further comprising an opening adjacent to the distal end of the insulating sheath for the delivery of fluid to tissue.

8. The device of claim 1, further comprising a fluid lumen formed through the elongate member and adapted to deliver fluid to tissue surrounding the insulating element.

9. The device of claim 8, further comprising a handle having a fluid port that is coupled to the fluid lumen.

10. The device of claim 1, wherein the energy emitter and the insulating element are rotatable relative to the elongate member.

11. A method for processing the device of claim 1 for surgery, comprising:
a) obtaining the device of claim 1;
b) sterilizing the device; and
c) storing the device in a sterile container.

12. The device of claim 1, wherein the energy emitter has a proximal end positioned distal to a proximal end of the insulating element and a distal end positioned proximal to a distal end of the insulating element such that the energy emitter is fully encapsulated by the insulating element.

13. The device of claim 1, wherein a distal end of the electrical connector extends into a bore formed in a proximal end of the energy emitter.

14. An endoscopic tissue resecting device, comprising:
- an elongate flexible shaft adapted to be inserted through a tortuous body lumen;
- an energy delivering electrode located distal to a distal end of the elongate shaft; and
- an insulating tip surrounding the electrode and having an opening formed therein for receiving energy from the electrode therethrough, the opening being configured to control a direction of energy delivery;
- wherein the energy delivering electrode and the insulating tip are rotatable relative to the elongate flexible shaft;
- wherein the electrode has an elongate substantially planar tip and the opening comprises an elongate slit formed in a distal end of the insulating tip for controlling a direction of energy emitted from the electrode.

15. The device of claim 14, further comprising an insulating sheath disposed within the elongate shaft and a lumen formed between the elongate shaft and the insulating sheath, the lumen being adapted to deliver fluid therethrough.

16. The device of claim 14, further comprising a fluid lumen formed through the elongate shaft and adapted to deliver fluid to tissue surrounding the insulating tip.

17. The device of claim 14, further comprising a handle coupled to a proximal end of the elongate flexible shaft, the handle having a rotating knob thereon for rotating the energy delivering electrode and the insulating tip relative to the elongate flexible shaft.

18. An endoscopic tissue resecting device, comprising:
- a handle;
- an elongate flexible shaft extending distally from the handle, the elongate flexible shaft being configured to be inserted through a tortuous body lumen, the elongate flexible shaft including
  - an electrical connector wire,
  - an insulating sheath disposed over the electrical connector wire, and
  - an outer tube disposed over the insulating sheath;
- an energy emitter assembly coupled to a distal end of the elongate flexible shaft, the energy emitter assembly including
  - an insulating tip positioned distal to a distal end of the outer tube and having a proximal opening formed therein that receives a distal end of the electrical connector wire therethrough, and a distal opening formed therein, and
  - an energy delivering electrode disposed within the insulating tip between the proximal and distal openings, the energy delivering electrode having a proximal end coupled to a distal end of the electrical connector wire, and a distal end configured to deliver energy through the distal opening in the insulating tip;
- wherein the energy emitter assembly is rotatable relative to the outer tube;
- wherein the electrode has an elongate substantially planar tip and the distal opening comprises an elongate slit formed in a distal end of the insulating tip for controlling a direction of energy emitted from the electrode.

* * * * *